(12) United States Patent
Heismann

(10) Patent No.: US 7,728,298 B2
(45) Date of Patent: Jun. 1, 2010

(54) DETECTOR BAR OR DETECTOR FORMED FROM A NUMBER OF DETECTOR BARS, AND COMPUTED-TOMOGRAPHY UNIT WITH SUCH A DETECTOR

(75) Inventor: Bjoern Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 199 days.

(21) Appl. No.: 11/287,360

(22) Filed: Nov. 28, 2005

(65) Prior Publication Data

US 2006/0124856 A1 Jun. 15, 2006

(30) Foreign Application Priority Data

Nov. 29, 2004 (DE) .................. 10 2004 057 533

(51) Int. Cl.
*G01T 1/00* (2006.01)

(52) U.S. Cl. .................. 250/363.05; 250/361 R; 250/363.02; 250/363.04; 250/370.09; 378/4; 378/13

(58) Field of Classification Search ............ 250/370.08, 250/370.11, 361 R–363.09; 378/4, 13
See application file for complete search history.

(56) References Cited

U.S. PATENT DOCUMENTS

| | | | | |
|---|---|---|---|---|
| 4,338,521 | A * | 7/1982 | Shaw et al. ............ | 250/370.11 |
| 5,955,733 | A | 9/1999 | Orava et al. | |
| 6,115,448 | A | 9/2000 | Hoffman | |
| 6,163,028 | A | 12/2000 | Orava et al. | |
| 6,396,898 | B1 * | 5/2002 | Saito et al. ............ | 378/19 |
| 6,472,668 | B1 | 10/2002 | Griesmer et al. | |
| 6,510,195 | B1 * | 1/2003 | Chappo et al. ......... | 378/19 |
| 6,621,084 | B1 * | 9/2003 | Wainer et al. ......... | 250/370.09 |
| 6,982,423 | B2 * | 1/2006 | Elgali ................. | 250/370.11 |
| 7,196,331 | B2 * | 3/2007 | Heismann ............. | 250/367 |
| 2002/0067796 | A1 * | 6/2002 | Hoffman .............. | 378/19 |
| 2006/0076498 | A1 * | 4/2006 | Hilderscheid et al. .. | 250/370.09 |
| 2006/0180769 | A1 * | 8/2006 | Hackenschmied et al. ............. | 250/370.09 |
| 2006/0231767 | A1 * | 10/2006 | Danzer et al. ......... | 250/370.11 |

FOREIGN PATENT DOCUMENTS

| | | |
|---|---|---|
| DE | 198 53 646 A1 | 5/1999 |
| EP | 0 847 596 B1 | 1/2004 |
| WO | WO 03/044563 A1 | 5/2003 |

OTHER PUBLICATIONS

German Office Action.

* cited by examiner

*Primary Examiner*—David P Porta
*Assistant Examiner*—Casey Bryant
(74) *Attorney, Agent, or Firm*—Harness, Dickey & Pierce, P.L.C.

(57) ABSTRACT

A detector bar, a detector formed from a number of detector bars, and a computed-tomography unit including such a detector is disclosed, each detector bar being formed from a number of individual modules. A detector bar has a module carrier for mechanically retaining the individual modules, and a printed circuit board, structurally separate from the module carrier, for making electric contact with the individual modules. The individual modules can thus be exchanged without disturbance, and simple aligning of the individual modules can thus be carried out while electric contact is simultaneously made.

31 Claims, 3 Drawing Sheets

DETECTOR BAR OR DETECTOR FORMED FROM A NUMBER OF DETECTOR BARS, AND COMPUTED-TOMOGRAPHY UNIT WITH SUCH A DETECTOR

The present application hereby claims priority under 35 U.S.C. §119 on German patent application number DE 10 2004 057 533.9 filed Nov. 29, 2004, the entire contents of which is hereby incorporated herein by reference.

FIELD

The invention generally relates to a detector bar or a detector that is formed from a number of detector bars. The invention further generally relates to a computed-tomography unit with such a detector.

BACKGROUND

EP 0 847 596 B1 discloses a detector for a tomography unit that is formed from a plurality of individual modules that are directly connected, both mechanically and electrically, to a component carrier assigned to the detector. Each individual module has detector elements arranged to form an array. The detector is constructed such that each individual module can be exchanged without being destroyed. The simultaneous embodiment of the electric and mechanical contact between the individual modules and a component carrier is, however, associated with a number of disadvantages, particularly given a requisite alignment of the individual modules relative to one another.

Making electric contact with the individual modules must be executed in such a way that an electric contact remains reliably made even given a displacement of the individual modules associated with the alignment. However, making electric contact with the component carrier in a way insensitive to displacement is associated with increased outlay on design and more complicated production processes for the corresponding contact elements (contact bump and contact surface).

Furthermore, in the known case a reliable electric contact between the component carrier and the individual module is possible only when the contact elements are held together with a certain expenditure of force. However, the mechanical interactions associated therewith complicate easy and precise alignment of the individual modules.

SUMMARY

It is an object of at least one embodiment of the present invention to configure a detector bar and/or a detector and/or a computed-tomography unit. In one example embodiment, this is done in such a way as to encourage or even ensure precise alignment of individual modules in a simple way in conjunction with simultaneous reliable electric contact.

An object of at least one embodiment may be achieved by a detector bar, by a detector, and/or by a computed-tomography unit.

According to at least one embodiment of the invention, the detector bar has a module carrier for mechanically retaining a number of individual modules, and a printed circuit board, separate from the module carrier, for making electric contact with the individual modules, the printed circuit board being arranged on the side of the module carrier opposite the individual modules.

Thus, by contrast with the known case, the mechanical retention of, and electric contact with, the individual modules are designed in a structurally separate fashion from one another in at least one embodiment of the present invention. Because of the separation of mechanical and electric functions, the individual modules can be aligned precisely in a simple way while there is simultaneously reliable contact with the individual modules. Disturbing mechanical interactions such as occur in the known case owing to electric contact being made with the individual modules are avoided.

In an advantageous refinement of at least one embodiment of the invention, electric contact is made by way of electric conductor tracks such that the individual modules can be displaced without hindrance in a particularly simple way while electric contact is simultaneously made, given an appropriate length and an appropriate flexibility of the electric conductor tracks. The electric conductor tracks can be so-called flex cables, for example.

Electric contact is preferably made in order to supply power to the individual modules and to transmit signals and control commands such that there is no need for additional data or power supply lines between the individual modules one among another.

Mechanical retention between the module carrier and the respective individual module is advantageously of releasable design such that the individual modules can easily be exchanged or mutually aligned without being destroyed. The individual modules can, in particular, be aligned even when electric contact is made with the individual modules.

For reasons of simplification, in what follows the side of the module carrier that faces the x radiation is denoted as front side, and the side of the module carrier correspondingly averted from the x radiation is denoted as rear side.

A screwed connection that is particularly easy to make may be provided, for example, for the mechanical retention between the individual modules on the module carrier. Thus, for example, it is conceivable for the module carrier respectively to have a cutout, for example in the form of a bore, and for the individual module respectively to have a thread matching the bore such that the two components can be connected by a screw that is guided into the thread of the individual module through the bore in the module carrier, starting from the rear side of the module carrier.

As an alternative to the screwed connection, it is also advantageously possible to provide a clamping apparatus by which the respective individual module can be rigidly connected to the module carrier through simply being plugged on.

In an advantageous refinement of at least one embodiment of the invention, the module carrier has a device/method/etc. for making electric contact with the individual modules so that it is possible for a cable to be guided simply between the respective individual module and the printed circuit board. In a very simple case, in order to make electric contact with the individual modules cutouts are provided in the module carrier that can be produced, for example, by milling, drilling or punching.

In an advantageous refinement of at least one embodiment of the invention, the module carrier is additionally equipped with at least one fastening device(s) that serve(s) to fasten the detector on a detector frame mechanically in a simple and reliable fashion.

The individual modules can advantageously be arranged in one dimension on the module carrier of a detector bar. Also conceivable, however, are configurations of a detector bar in the case of which the individual modules are to be arranged on the module carrier in two-dimensional form. Which of the two arrangements of the individual modules is selected can depend, for example, on the type of use and the required detector surface of a detector.

Each individual module can advantageously have electronic components for signal amplification, for voltage conditioning or for decoupling interference signals. Each individual module may include, for example, an array of detector elements that are retained on a substrate, for example ceramic.

Installing device(s) may be provided on the module carrier advantageously facilitate the positioning of the individual modules on the module carrier when the detector bar is being constructed. In a particularly simple design, the installing device(s) can be marking lines that respectively indicate a boundary line between neighboring individual modules. However, instead of the marking line it is also possible to provide recesses in the module carrier in which the individual modules are to be inserted during installation.

In an advantageous refinement of at least one embodiment of the invention, each of the detector elements is a directly converting semiconductor. It is likewise conceivable as an alternative to this for each of the detector elements to comprise a scintillator and a photodiode. It can likewise be expedient for the purpose of collimating the incident x radiation to assign each individual module a collimator.

BRIEF DESCRIPTION OF THE DRAWINGS

Example embodiments of the invention and further advantageous refinements of the invention in accordance with the subclaims are illustrated schematically in the following drawings, in which:

DETAILED DESCRIPTION OF THE EXAMPLE EMBODIMENTS

Figure 1:
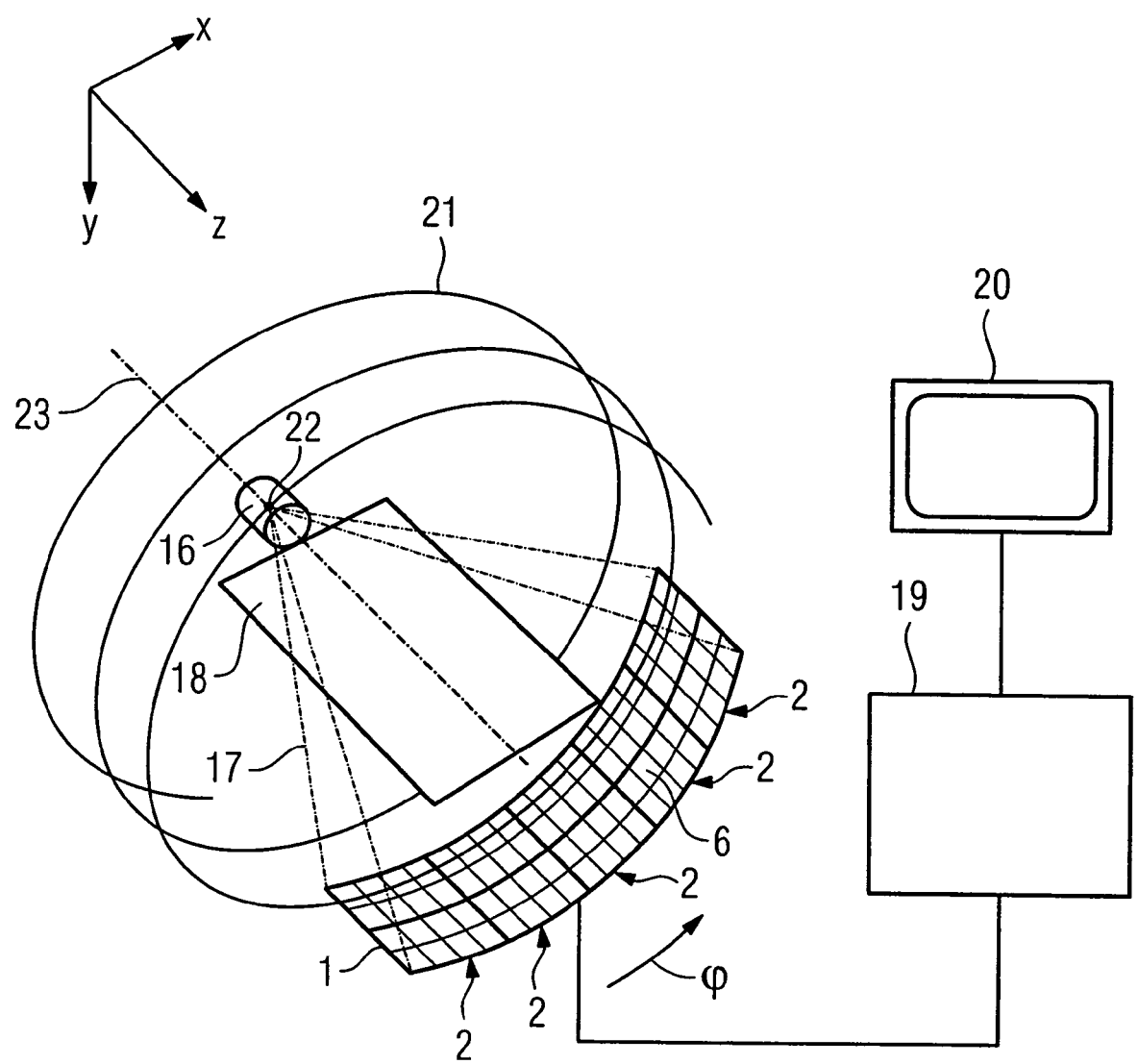
FIG. 1 shows an illustration of a computed-tomography unit that is partially perspective and partially in the form of a block diagram.

FIG. 1 shows an illustration of a computed-tomography unit that is partially perspective and partially in the form of a block diagram. The computed-tomography unit includes a holding system having an x-ray emitter 16 and a detector 1 that is formed from a number of detector bars 2, each of the detector bars 2 having a plurality of individual modules 5 that are arranged in the z-direction of a coordinate system illustrated in FIG. 1. The computed-tomography unit further has a computing device 19 for processing the detector output signals generated by the detector 1, and a display unit 20 for displaying a result image.

The x-ray emitter 16 and the detector 1 are fitted opposite one another on a rotatable detector frame (not illustrated) in such a way that during operation of the computed-tomography unit an x-ray beam emanating from a focus 22 of the x-ray emitter 16 and delimited by edge rays 17 impinges on the detector 1.

The detector frame can be set rotating about a rotation axis 23 in the φ-direction shown, via a drive device (not illustrated). The rotational axis 23 runs in this case parallel to the z-axis of the rectangular coordinate system shown. For a recording area of an object, for example a patient, supported on a support table 18, it is possible in this way to prepare x-ray pictures from different projection directions and/or rotary angle positions for the purpose of reconstructing a number of tomograms. In this case, the recording area can also be subjected to spiral scanning 21 by way of continuously feeding the support table 18 in the direction of the z-axis, given simultaneous rotation of the recording system 16.1 about the recording area to be examined.

Each x-ray picture includes the detector output signals generated by the detector 1, which are a measure of the attenuation of the x radiation passing through the recording area. The detector output signals are fed to the computing device(s) 19 where, depending on the operating mode of the computed-tomography unit, they are converted by calculation into tomograms or volumetric images using a reconstruction method known per se.

Figure 2:
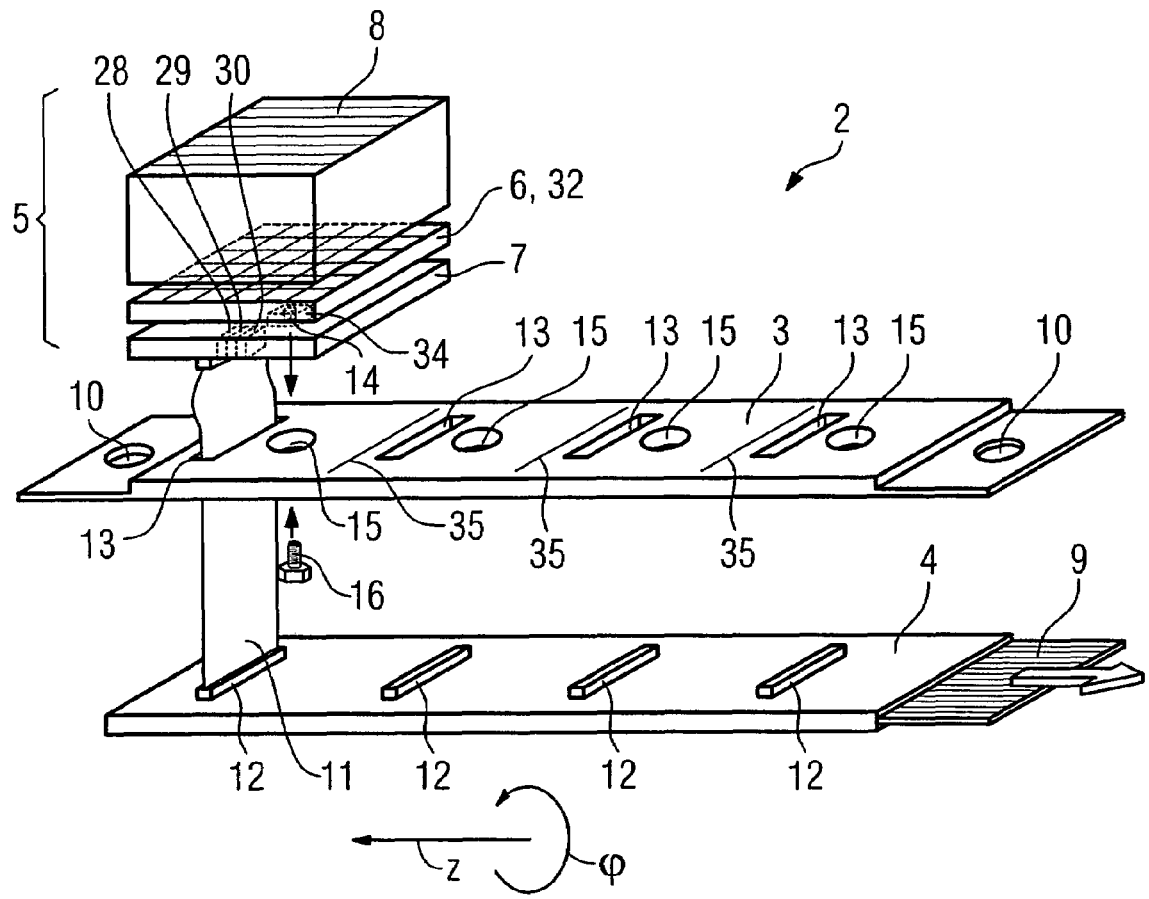
FIG. 2 shows an exploded illustration, shown in perspective, of a detector bar according to an embodiment of the invention.

A detector bar 2 according to at least one embodiment of the invention that can be used, for example, to construct a detector 1, shown in FIG. 1, of the computed-tomography unit is shown in an exploded, perspective illustration in FIG. 2. The detector bar 2 is formed from a number of individual modules 5, only one of the individual modules 5 being illustrated in FIG. 2, for reasons of clarity. Typical dimensions of such an individual module 5 are in a range from 1 cm×1 cm to 10 cm×10 cm in the z- and φ-directions shown. In depth, the individual module 5 extends between 1 mm and 15 cm, by way of example. The individual modules 5 are arranged sequentially in one dimension on a common module carrier 3 and mechanically retained thereon and electrically connected to a printed circuit board 4 designed to be structurally separate from the module carrier 3.

Each of the individual modules 5 has an array of detector elements 6 that are retained on a substrate 7, for example ceramic. The detector elements 6 serve to generate detector output signals that are a measure of the absorption of the x radiation emanating from the x-ray emitter 16 in FIG. 1, for example an x-ray tube, and passing through a recording area.

In the example shown, the x radiation impinging on a detector element 6 is converted into a detector output signal by a directly converting semiconductor 32. The x radiation can, however, also be converted by means of a scintillator 24, assigned to the respective detector element 6 and shown in FIG. 3, and of a photodiode 25 that is optically coupled to the scintillator 24. It is expedient to assign each individual module 5 a collimator 8 such that a detector element 6 respectively detects the x radiation of a specific solid angle.

In this example, electronic components 28, 29, 30 for voltage conditioning, for signal amplification and for decoupling interference signals by way of capacitors are provided on the side of the substrate 7 averted from the x-radiation and denoted below as rear side. The electronic components 28, 29, 30 need not, however, necessarily be assigned to the substrate 7 or to the individual module 5. It would also be conceivable for at least a portion of the electronic components 28, 29, 30 to be arranged on the printed circuit board 4 or on an electronic apparatus assigned to the detector frame.

At least one thread 14 is provided for the individual module 5, in order to produce a mechanical connection between the individual module 5 and the module carrier 3 by use of a screwed connection. The thread 14 can expediently be recessed into a small aluminum block 34 that is an integral constituant of the substrate 7. Furthermore, a connecting cable 11, for example a flex cable, for making electric contact between the individual module 5 and the printed circuit board 4 is mounted on the rear side of the respective individual module 5. The connecting cable 11 is in permanent soldered connection with the individual module 5 and with the electronic components 28, 29, 30 provided thereon. It is, of course, also conceivable for the connecting cable 11 to be releasably fitted onto the individual module 5 in the form of a plug-in connection.

Figure 4:
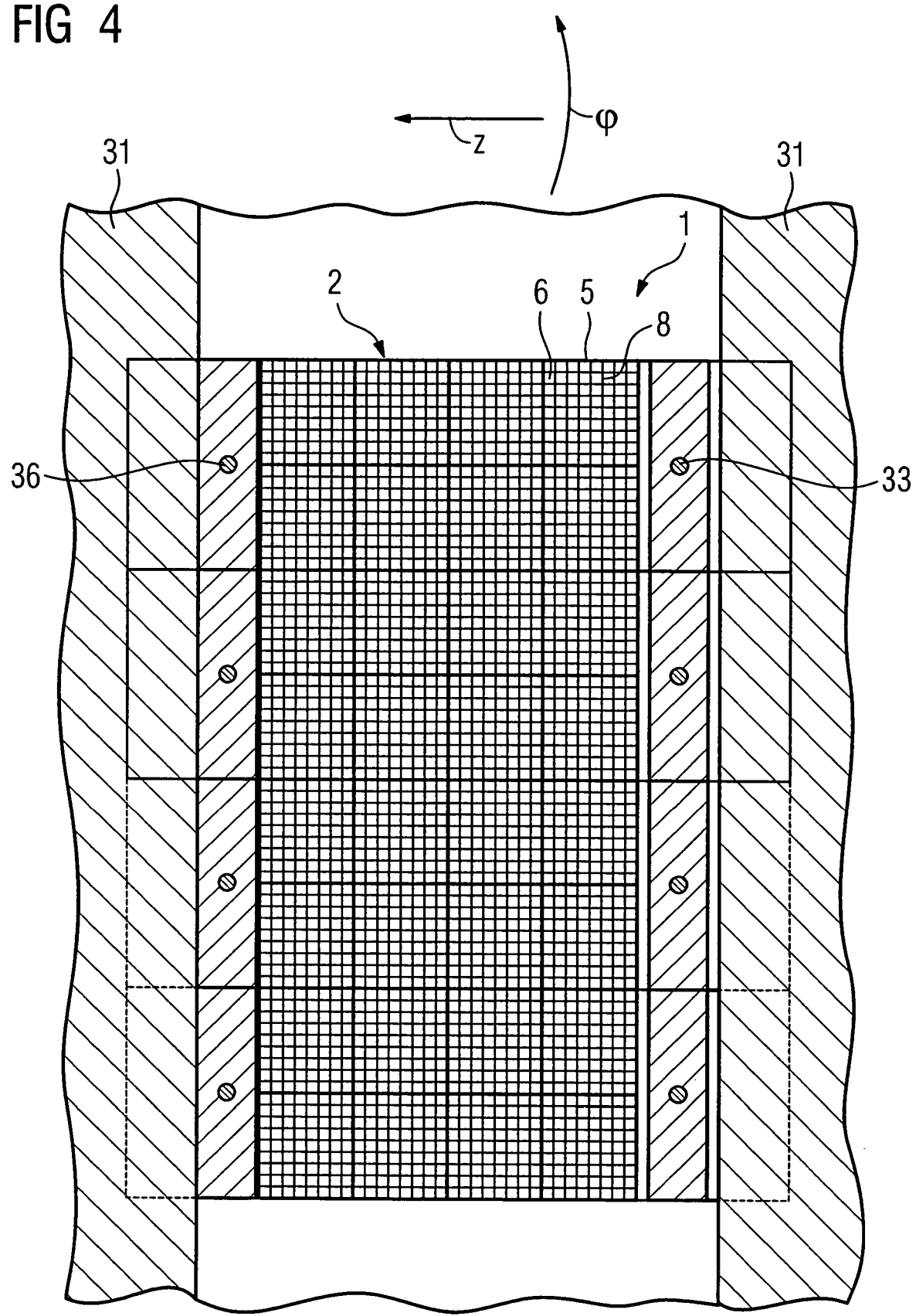
FIG. 4 shows a plan view of a detail of a detector according to an embodiment of the invention with a number of detector bars on a detector frame.

A cutout 15 assigned to a thread 14 of the individual module 5 is respectively provided on the module carrier 3 such that the individual modules 5 can be screwed with the module carrier 3 in order to produce a mechanical connection. A screw 16 is respectively screwed for this purpose through the cutout 15 into the thread 14 of the individual module 5 from the rear side of the module carrier 3. A screwed connection offers the advantage, in particular, that the mechanical connection can easily be released again for the purpose of mutually aligning or of exchanging the individual modules 5. However, it is not only screwed connections that are suitable for producing a mechanical connection, but also, as shown in FIG. 4, plug-in connections 26, 27, for example so-called slot and feather connections.

The module carrier 3 has installing device(s) 35, for example in the form of marking lines, applied to the surface of the module carrier, such that the individual modules 5 can be fitted into the module carrier 3 in accurate positions. Moreover, device(s) 13 for making the electric contact or for guiding through the connecting cable 11 of the individual modules 5 are provided in the module carrier 3. In the example shown, the device(s) 13 include longitudinally directed cutouts that serve for guiding through the connecting cable 11 respectively proceeding from the individual module 5.

Moreover, arranged on the module carrier 3 are fastening device(s) 10 that enable the module carrier 3 or the detector bar 2 to be fastened on a detector frame. In the example from FIG. 2, the module carrier is provided with fastening device(s) 10 in the form of bores that serve for producing a screwed connection. However, fastening device(s) 10 of other types, for example a plug-in connection, can also be used.

The module carrier 3 is preferably produced from metal. However, any other desired materials can also be used in principle. The essential thing is merely that the module carrier 3 has a certain stiffness such that the high acceleration forces occurring as the recording system rotates during operation of the computed-tomography unit do not displace the individual modules from the position on the module carrier 3.

The printed circuit board 4 is designed to be structurally separate from the module carrier 3, and is also not necessarily mechanically connected to the latter. The printed circuit board 4 is electrically connected in a flexible fashion to the individual modules 5, and can, for example, be plugged into an electronic apparatus, assigned to the detector frame, via a connection 9 provided therefor. The electric connection between the connecting cable 11 and the printed circuit board 4 is of releasable design, for example in the form of a plug-in connection 12.

The mechanical retention of the individual modules 5, and the making of their electric contact are designed separately from one another such that, in the case of an alignment of the individual modules 5 relative to one another, no disturbing mechanical interactions occur when electric contact is made for the individual modules 5, such as can happen given the abovenamed detector structure. Rather, the alignment of the individual modules 5 can be designed independently of the electric contact. Thus, for example, it is conceivable that, with electric contact released, the individual modules 5 are accurately aligned in a first installation step for constructing the respective detector bar 2, and the individual modules 5 are electrically contacted by plugging the connecting cables 11 into a plug-in connection 12 provided therefor on the printed circuit board in a second installation step.

The individual modules 5 are supplied with power, and signals, in particular detector output signals, and control commands are transmitted via the connecting cable 11. The connecting cable 11 is connected to the electric connection 9 on the printed circuit board 4 which makes the connection to an electronic apparatus (not illustrated) assigned to the detector frame.

Figure 3:
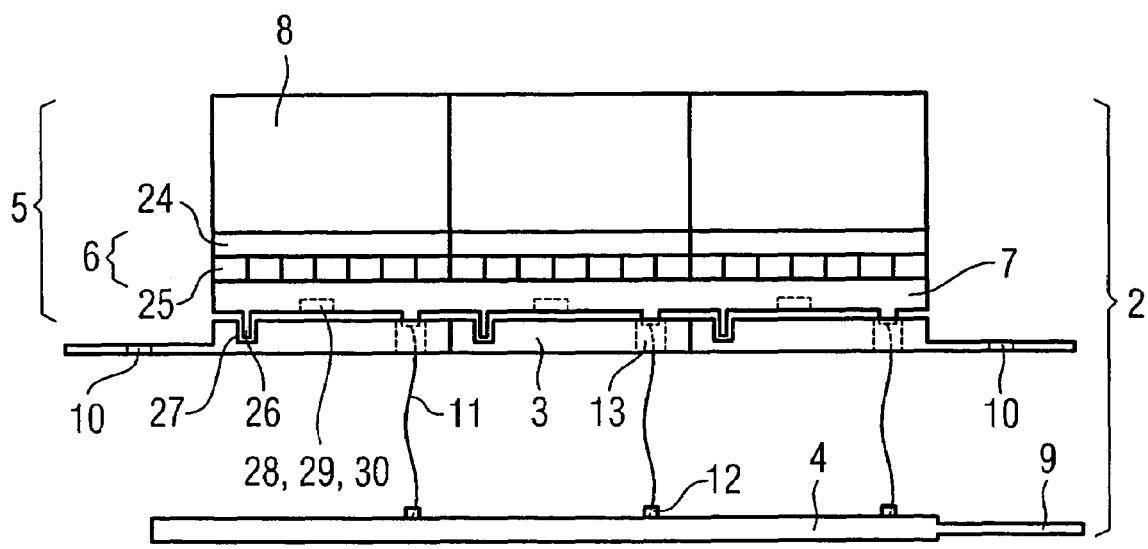
FIG. 3 shows a side view of the detector bar from FIG. 2, but with a mechanical connection in the form of a plug-in connection, and detector elements that have a scintillator and a photodiode.

The inventive detector bar 2 from FIG. 2 is illustrated in a side view in FIG. 3. However, by contrast with FIG. 2, instead of a directly converting semiconductor each detector element 6 has a scintillator 24 and a photodiode 25 optically coupled thereto. Moreover, the mechanical connection between the respective individual module 5 and the module carrier 3 is implemented not by way of screwed connections 14, 15, 16, but by plug-in connections 26, 27, each plug-in connection 26, 27 being formed from alignment pins 26, on the side of the individual module, and alignment bores 27, on the side of the module carrier.

FIG. 4 shows a plan view of a detail of a detector 1 according to at least one embodiment of the invention, which has a plurality of detector bars 2 retained on a detector frame 31. Each detector bar 2 in this case usually forms a segment of a curved cylinder lateral surface. A number of detector bars arranged next to one another therefore define a cylindrical detector surface that has an extent matched to an examination. Each detector bar 2 is formed from a plurality of individual modules 5, the individual modules 5 being arranged in two dimensions on a module carrier 3 (not visible). Likewise not visible is the making of electric contact (designed in a fashion structurally separate therefrom) between the individual modules 5 and the printed circuit board 4. For reasons of clarity, only one component of the detector bar 2 is provided with reference numerals. The individual modules 5 are screwed to the detector frame 31 via the detector frame screws 33 arranged on the side of the detector bar 2.

In addition to the alignment, shown in FIG. 4, of the detector bar in the z-direction, it is likewise conceivable that the detector bar can be aligned in the $\phi$-direction. The detector is also not necessarily formed from a plurality of detector bars. It can certainly also be advantageous when the detector is formed only from a single detector bar. Alignment of the detector bars relative to one another is eliminated in this case.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector bar, comprising:
   a number of individual modules, each comprising an array of detector elements;
   a module carrier for mechanically retaining the individual modules, the module carrier being positioned on a side of the individual modules opposite to a side on which x-ray radiation impinges; and
   a printed circuit board, embodied separately from said module carrier, for making electric contact with the individual modules and an external electric apparatus, the printed circuit board being arranged on a side of the module carrier opposing the side on which the individual modules are positioned, wherein said electric contact between the printed circuit board and each individual module is made via flexible electric conductor tracks, the flexible electric conductor tracks being guided through cut-outs provided in the module carrier, said electric contact between the printed circuit board and the external electric apparatus is made via a separate electrical connection.

2. The detector bar as claimed in claim 1, wherein electric contact is made in order to supply power to the individual modules and to transmit signals and control commands.

3. The detector bar as claimed in claim 1, wherein mechanical retention between the module carrier and the respective individual module is of releasable design.

4. The detector bar as claimed in claim 1, wherein a screwed connection is provided for the mechanical retention between the module carrier and the respective individual module.

5. The detector bar as claimed in claim 1, wherein a clamping apparatus is provided for the mechanical retention between the module carrier and the respective individual module.

6. The detector bar as claimed in claim 1, wherein the module carrier includes fastening means for mechanically fastening the detector bar on a detector frame.

7. The detector bar as claimed in claim 1, wherein the module carder includes an installing device.

8. The detector bar as claimed in claim 7, wherein the installing device is a marking line.

9. The detector bar as claimed in claim 1, wherein the individual modules are arranged in one dimension on the module carrier.

10. The detector bar as claimed in claim 1, wherein the individual modules are arranged in two dimensions on the module carrier.

11. The detector bar as claimed in claim 1, wherein each individual module has electronic components for at least one of signal amplification, voltage conditioning and decoupling interference signals.

12. The detector bar as claimed in claim 1, wherein each of the detector elements is a directly converting semiconductor.

13. The detector bar as claimed in claim 1, wherein each of the detector elements includes a scintillator and a photodiode.

14. The detector bar as claimed in claim 1, wherein each individual module includes a collimator.

15. The detector bar of claim 1, wherein the individual modules, the module carrier and the printed circuit board are arranged vertically in a path of x-ray radiation.

16. The detector bar of claim 1, wherein the individual modules, the module carrier and the printed circuit board are stacked vertically.

17. The detector bar of claim 1, wherein each individual module electrically contacts the printed circuit board via a separate flexible electric conductor track guided through a separate cut-out provided in the module carrier.

18. The detector bar of claim 1, wherein the detector bar is connectable to a detector frame positioned at a side of the detector bar opposite to the side at which the individual modules are arranged.

19. A detector comprising:
a plurality of detector bars, each detector bar including,
a number of individual modules, each comprising an array of detector elements;
a module carrier for mechanically retaining the individual modules, the module carrier being positioned on a side of the individual modules opposite to a side on which x-ray radiation impinges; and
a printed circuit board, embodied separately from said module carrier, for making electric contact with the individual modules and an external electric apparatus, the printed circuit board being arranged on a side of the module carrier opposing the side on which the individual modules are positioned, wherein
said electric contact between the printed circuit board and each individual module is made via flexible electric conductor tracks, the flexible electric conductor tracks being guided through cut-outs provided in the module carrier, and
said electric contact between the printed circuit board and the external electric apparatus is made via a separate electrical connection.

20. A computed-tomography unit comprising a detector as claimed in claim 19.

21. A computed-tomography unit comprising an x-ray emitting device and a detector as claimed in claim 19.

22. The detector of claim 19, wherein each individual module electrically contacts the printed circuit board via a separate flexible electric conductor track guided through a separate cut-out provided in the module carrier.

23. The detector of claim 19, wherein each detector bar is connectable to a detector frame positioned at a side of each detector bar opposite to the side at which the individual modules are arranged.

24. A detector bar for use in a computed-tomography unit, the detector bar comprising:
a module carrier having a plurality individual detector modules mechanically fixed thereto, the plurality of detector modules being arranged on a first side of the module carrier; and
a printed circuit board, separate from said module carrier, for making electric contact with the individual modules and an external electric apparatus, the printed circuit board being arranged on a second side of the module carrier, the second side opposing the first side, wherein
said electric contact between the printed circuit board and each individual module is made via flexible electric conductor tracks, the flexible electric conductor tracks being guided through cut-outs provided in the module carrier, and
said electric contact between the printed circuit board and the external electric apparatus is made via a separate electrical connection.

25. The detector bar as claimed in claim 24, wherein electric contact is made in order to supply power to the individual modules and to transmit signals and control commands.

26. The detector bar as claimed in claim 24, wherein mechanical retention between the module carrier and the respective individual module is of releasable design.

27. A computed-tomography unit comprising a detector as claimed in claim 24.

28. A detector comprising at least one detector bar, retained on a detector frame, as claimed in claim 24.

29. A computed-tomography unit comprising an x-ray emitting device and a detector as claimed in claim 28.

30. The detector bar of claim 24, wherein each individual module electrically contacts the printed circuit board via a separate flexible electric conductor track guided through a separate cut-out provided in the module carrier.

31. The detector bar of claim 24, wherein the detector bar is connectable to a detector frame positioned at a side of the detector bar opposite to the side at which the individual modules are arranged.

* * * * *